(12) United States Patent
Birrell

(10) Patent No.: US 9,168,302 B2
(45) Date of Patent: Oct. 27, 2015

(54) REDUCTION OF SIDE EFFECTS FROM AROMATASE INHIBITORS USED FOR TREATING BREAST CANCER

(75) Inventor: Stephen N. Birrell, Medindie (AU)

(73) Assignee: Chavah Pty Ltd, Medindie, South Australia (AU)

(*) Notice: Subject to any disclaimer, the term of this patent is extended or adjusted under 35 U.S.C. 154(b) by 313 days.

(21) Appl. No.: 13/354,103

(22) Filed: Jan. 19, 2012

(65) Prior Publication Data

US 2012/0122824 A1    May 17, 2012

Related U.S. Application Data

(63) Continuation of application No. 12/083,771, filed as application No. PCT/AU2006/001539 on Oct. 18, 2006, now abandoned.

(60) Provisional application No. 60/732,662, filed on Nov. 3, 2005, provisional application No. 60/798,308, filed on May 8, 2006.

(30) Foreign Application Priority Data

Oct. 19, 2005 (AU) ................ 2005905768

(51) Int. Cl.
| | |
|---|---|
| A01N 45/00 | (2006.01) |
| A61K 31/56 | (2006.01) |
| A61K 45/06 | (2006.01) |
| A61K 31/4196 | (2006.01) |
| A61K 31/568 | (2006.01) |

(52) U.S. Cl.
CPC ............. *A61K 45/06* (2013.01); *A61K 31/4196* (2013.01); *A61K 31/568* (2013.01)

(58) Field of Classification Search
USPC ................................. 514/170, 178
See application file for complete search history.

(56) References Cited

U.S. PATENT DOCUMENTS

| | | | |
|---|---|---|---|
| 4,147,783 | A | 4/1979 | van der Vies |
| 5,861,387 | A * | 1/1999 | Labrie et al. .............. 514/169 |
| 6,696,432 | B1 | 2/2004 | Elliesen et al. |
| 2003/0087885 | A1 | 5/2003 | Masini-Eteve et al. |
| 2004/0191311 | A1 | 9/2004 | Liang et al. |
| 2005/0176692 | A1 * | 8/2005 | Amory et al. .............. 514/171 |
| 2005/0233970 | A1 | 10/2005 | Garnick |
| 2006/0069067 | A1 * | 3/2006 | Bhatnagar et al. ............. 514/89 |

FOREIGN PATENT DOCUMENTS

| | | |
|---|---|---|
| JP | 4-504848 | 8/1992 |
| JP | 8-505629 | 6/1996 |
| JP | 2003-512301 | 4/2003 |
| WO | WO 90/10462 | 9/1990 |
| WO | WO 94/16709 | 8/1994 |
| WO | WO 00/69467 | 11/2000 |
| WO | WO01/87334 | 11/2001 |
| WO | WO02/30355 | 4/2002 |
| WO | WO2005/011705 | 2/2005 |
| WO | 2005/037263 | 4/2005 |
| WO | WO 2005/037263 | 4/2005 |
| WO | WO 2005/070434 | * 8/2005 |

OTHER PUBLICATIONS

Goss et. al. (Oncology (1997) 11:1697-1703).*
International Search Report dated Jan. 3, 2007 for PCT/AU2006/001539.
The Merck Index, 13th ed., Merck & Co., Inc. (2001), Entry Nos. 632 (p. 105), 3944 (p. 692) and 9255 (p. 1638).
Goss, Paul E., et al. "Anastrozole: A New Selective Nonsteroidal Aromatase Inhibitor" *Oncology*, vol. 11. No. 11 (Nov. 1, 1997) pp. 1697-1703—Abstract only (Complete from www.cancernetwork.com).
Santen, Richard J. "Recent Progress in Development of Aromatase Inhibitors" *J. Steroid Biochem. Molec. Biol.*, vol. 37, No. 6 (1990) pp. 1029-1035.
Wasaff, Barbara "Current Status of Hormonal Treatments for Metastatic Breast Cancer in Postmenopausal Women" *Oncol. Nurs. Forum*, vol. 24, No. 9 (1997) pp. 1515-1520.
European Search Report dated Aug. 24, 2009 for EP 1945224.
Rhoden, International Journal of Importence Research (2004) 16:95-97.
Somboonporn, et al., "Postmenopausal Testosterone Therapy and Breast Cancer Risk," Maturitas, 49, 267-275 (2004).
The North American Menopause Society, Menopause: The Journal of the North American Menopause Society, 12(5):497-511 (2005).
Japanese Office Action dated Jul. 3, 2012 for Application No. 2008-535845 with English Translation.
Rinsho et al., Japanese Journal of Clinical and Experimental Medicine, 70, 11, 3428-3433, 1993.

* cited by examiner

*Primary Examiner* — Marcos Sznaidman
(74) *Attorney, Agent, or Firm* — Jones Day

(57) ABSTRACT

The present invention is directed generally to pharmaceutical compositions, methods, and kits for improving side effects associated with aromatase inhibitor treatment in a subject diagnosed with breast cancer. More specifically, the present invention provides compositions, methods, and kits comprising an aromatase inhibitor and an androgenic agent.

14 Claims, 8 Drawing Sheets

FIGURE 8. Items and layout of the endocrine subscale for the FACT-B.
Please indicate how true each statement has been for you *during the past 7 days*.

| Endocrine symptom subscale | Not at all | A little bit | Some-what | Quite a bit | Very much |
|---|---|---|---|---|---|
| I have hot flushes | 0 | 1 | 2 | 3 | 4 |
| I have cold sweats | 0 | 1 | 2 | 3 | 4 |
| I have night sweats | 0 | 1 | 2 | 3 | 4 |
| I have vaginal discharge | 0 | 1 | 2 | 3 | 4 |
| I have vaginal itching/irritation | 0 | 1 | 2 | 3 | 4 |
| I have vaginal bleeding or spotting | 0 | 1 | 2 | 3 | 4 |
| I have vaginal dryness | 0 | 1 | 2 | 3 | 4 |
| I have pain or discomfort with intercourse | 0 | 1 | 2 | 3 | 4 |
| I have lost interest in sex | 0 | 1 | 2 | 3 | 4 |
| I have gained weight | 0 | 1 | 2 | 3 | 4 |
| I feel lightheaded/dizzy | 0 | 1 | 2 | 3 | 4 |
| I have been vomiting | 0 | 1 | 2 | 3 | 4 |
| I have diarrhea | 0 | 1 | 2 | 3 | 4 |
| I get headaches | 0 | 1 | 2 | 3 | 4 |
| I feel bloated | 0 | 1 | 2 | 3 | 4 |
| I have breast sensitivity/tenderness | 0 | 1 | 2 | 3 | 4 |
| I have mood swings | 0 | 1 | 2 | 3 | 4 |
| I am irritable | 0 | 1 | 2 | 3 | 4 |

REDUCTION OF SIDE EFFECTS FROM AROMATASE INHIBITORS USED FOR TREATING BREAST CANCER

CROSS-REFERENCES TO RELATED APPLICATIONS

This application is a continuation of U.S. application Ser. No. 12/083,771, filed May 6, 2009, which is the National Phase application of International Application No. PCT/AU2006/001539, filed Oct. 18 2006 which claims the priority benefit of the following applications: 1) Australian Provisional Serial No. 2005905768, filed on Oct. 19, 2005, 2) U.S. Provisional Ser. No. 60/732,662, filed Nov. 3, 2005, and 3) U.S. Provisional Ser. No. 60/798,308, filed May 8, 2006. These applications, in their entirety, are incorporated herein by reference.

FIELD OF THE INVENTION

The present invention relates to the reduction of side effects caused by aromatase inhibitors which are used to treat subjects with breast cancer. In particular, the present invention provides compositions, methods, and kits for reducing side effects in post-menopausal women with breast cancer already being treated with aromatase inhibitor comprising administering an effective amount of an androgenic agent. Furthermore, the present invention provides compositions, methods, and kits for reducing side effect's associated with aromatase inhibitor treatment in post-menopausal women with breast cancer comprising administering a pharmaceutical composition comprising an aromatase inhibitor and an androgenic agent.

BACKGROUND OF THE INVENTION

Breast cancer is the most common non-cutaneous malignancy in women. It is estimated that there were 212,600 new cases in 2003 in the USA. It is estimated that at least 13% of women will develop breast cancer at some time in their life, and this incidence is increasing. As more than 80% of breast tumors grow in response to sex hormone stimulation caused by estrogen, part of adjuvant therapy (i.e. therapy in addition to surgical removal of the tumor) is to administer an agent to block this growth stimulation, including by means of blocking estrogen receptor activation or blocking estrogen production.

One such agent has been tamoxifen. Notwithstanding its success in adjuvant breast cancer therapy, tamoxifen has unwanted side-effects, which can be categorized into estrogen receptor stimulating (uterine cancer, deep venous thrombosis) and estrogen receptor antagonizing (vaginal dryness, hot flushes, mood swings) and has led to the search for a better alternative. A more selective estrogen receptor regulator has so far not been successful in taking the place of tamoxifen and the current trend in hormonal therapy is to reduce the level of bio-available estrogen.

Another such agent has been aminoglutethimide (Cash, Brough et al 1967). This drug was poorly tolerated and resulted in a marked adrenal suppression that limited the use of the drug.

Over the past 15 years, however, more specific enzyme inhibitors have been developed, which specifically inhibit the aromatase enzyme that converts testosterone to estradiol. These compounds are known as aromatase inhibitors. They are used to block the conversion of testosterone to estradiol, resulting in non-tissue-specific enzymatic inhibition and almost complete ablation of testosterone conversion to estradiol. The relevant conversion pathways are shown in FIG. 1.

The development of these aromatase inhibitors, such as exemestane (Aromasin®), anastrozole (Arimidex®) and letrozole (Femara®) has brought about a major change in the therapeutic approach to patients with hormone-sensitive breast cancer. In randomized clinical trials, each of these aromatase inhibitors has demonstrated efficacy in the adjuvant treatment of post-menopausal women with receptor-positive tumors. Although long-term follow up for safety and overall survival continues in each of these trials, currently available data suggest that an aromatase inhibitor should now be included as part of adjuvant endocrine therapy for the great majority of receptor-positive post-menopausal patients. The current strategy comprises at least five years of global estrogen deprivation with a tissue non-specific aromatase inhibitor. These aromatase inhibitors overcome the significant adrenal toxicity of the previous anti-estrogen medications, and this has allowed them to now become the most widely prescribed hormonal therapy for breast cancer.

A significant problem with these aromatase inhibitors, however, is that they cause unwanted and substantial short and long-term side effects. Examples of these side effects include, but are not limited to, vasodilatation, osteoporosis, osteopenia, loss of libido, weight gain, vaginal dryness, sleeping difficulties, night sweats, asthenia, painful intercourse, pain, arthritis, arthralgia, breast pain, pharyngitis, depression, bloating, nausea, rash, mood swings, headache, diminished cognitive function, hypertension, insomnia, lymphoedema, back pain, peripheral edema, cold sweats, abdominal pain, injury, constipation, coughing, diarrhea, fracture, hypercholesteremia, infection, arthrosis, dizziness, dyspnea, paraesthesia, urinary tract infection, vulvovaginitis, anxiety, bone pain, chest pain, dyspepsia, flu syndrome, gastrointestinal disorder, sweating and/or leukorrhea.

The present invention described herein differs from other hormonal therapy methods for the treatment of breast cancer. It provides the advantages of androgen replacement therapy in combination with an aromatase inhibitor.

Current therapeutic circumstances in which an aromatase inhibitor (e.g., Arimidex®) and an androgenic agent (e.g., testosterone) have been used in combination previously are to reduce the estrogenic effect of testosterone abuse in body building, in particular gynaecomastia (Hoffmann J Raatamess N Journal of Sports Science and Medicine 5, 182-183 (2006), to reduce estrogenic side-effects in hypogonadal men on T therapy (Leder et al. 2004, and Leder et al. 2005), and to explore the safety issues (risk of cardiovascular disease) of androgen replacement therapy, specifically in female to male transexuals undergoing testosterone therapy. (Bunck et al. 2006). None of these circumstances of androgen replacement therapy, however, were for the treatment of a woman diagnosed with breast cancer. In fact, there has been a great reluctance by the medical profession to prescribe hormone substrates to women who have hormonally active breast cancers. The use of androgen replacement is controversial in post-menopausal women generally, and its use in women who have had breast cancer is almost universally contra-indicated. For example, a Proctor & Gamble application to the FDA for the Intrinsa product cited breast cancer as an absolute contra-indication to using the Intrinsa patch because of the concern about the testosterone being converted to estradiol and being used as a growth substrate by the malignancy (Shifren J L et al Testosterone patch for the treatment of hypoactive sexual desire disorder in naturally menopausal women: results from the INTIMATE NM1 study Menopause (in press).

Regardless of such medication, the conventional understanding remains that androgen (e.g., testosterone) replacement should be avoided in breast cancer subjects for fear of spurring tumor regrowth.

The present invention, however, goes against this conventional wisdom of not prescribing androgenic agents to women diagnosed with breast cancer. The present invention provides a novel therapy to alleviate side-effects of and/or to enhance the efficacy of aromatase inhibitor therapy in breast cancer treatment by supplementing and/or combining an aromatase inhibitor with an androgenic agent.

SUMMARY OF THE INVENTION

The present invention is directed generally to pharmaceutical compositions, methods, and kits for improving side effects associated with aromatase inhibitor treatment in a subject diagnosed with breast cancer.

One aspect of the present invention provides a pharmaceutical composition for improving a side effect associated with aromatase inhibitor treatment in a subject diagnosed with breast cancer comprising (a) an effective amount of an androgenic agent and (b) an effective amount of an aromatase inhibitor. Optionally, the pharmaceutical composition may comprise a pharmaceutically acceptable excipient and/or carrier.

Another aspect of the present invention provides a pharmaceutical composition for improving one or more side effects associated with aromatase inhibitor treatment in a subject diagnosed with breast cancer comprising an effective amount of an androgenic agent, and optionally a pharmaceutically acceptable excipient and/or carrier.

A further aspect of the present invention is a method for improving one or more side effects associated with aromatase inhibitor treatment in a subject diagnosed with breast cancer comprising administering to a subject a pharmaceutical composition comprising (a) an effective amount of an androgenic agent and (b) an effective amount of an aromatase inhibitor, and, optionally, a pharmaceutically acceptable excipient and/or carrier.

Another aspect of the present invention is a method for improving one or more side effects associated with aromatase inhibitor treatment in a subject diagnosed with breast cancer comprising administering to a subject a pharmaceutical composition comprising an effective amount of an androgenic agent and, optionally, a pharmaceutically acceptable excipient and/or carrier.

An additional aspect of the present invention is a method for improving the health of a subject with breast cancer having one or more side effects associated with aromatase inhibitor therapy comprising administering a pharmaceutical comprising an effective amount of an androgenic agent, and, optionally, a pharmaceutically acceptable excipient and/or carrier; or an effective amount of an androgenic agent, an effective amount of an aromatase inhibitor, and, optionally, a pharmaceutically acceptable excipient and/or carrier.

Another aspect of the present invention provides methods of manufacturing pharmaceutical compositions for improving one or more side effects associated with aromatase inhibitor treatment in a subject diagnosed with breast cancer comprising selecting an androgenic agent.

Furthermore, an aspect of the present invention is a kit for improving one or more side effects associated with aromatase inhibitor treatment in a subject diagnosed with breast cancer comprising an androgenic agent, an aromatase inhibitor, and instructions.

Another aspect of the present invention is a method for enhancing the efficacy of aromatase inhibitors comprising administering a pharmaceutical composition of the present invention Another aspect of the present invention is a method for increasing the bioavailability of an androgenic agent comprising administering a pharmaceutical composition of the present invention.

One aspect of the present invention provides a pharmaceutical composition for improving a side effect associated with an aromatase inhibitor such as third generation aromatase inhibitor treatment in a subject diagnosed with breast cancer comprising (a) an effective amount of an androgenic agent and (b) an effective amount of a such third generation aromatase inhibitor. Optionally, the pharmaceutical composition may comprise a pharmaceutically acceptable excipient and/or carrier.

A further aspect of the present invention is a method for improving one or more side effects associated with an aromatase inhibitor such as third generation aromatase inhibitor treatment in a subject diagnosed with breast cancer comprising administering to a subject a pharmaceutical composition comprising (a) an effective amount of an androgenic agent and (b) an effective amount of a third generation aromatase inhibitor, and, optionally, a pharmaceutically acceptable excipient and/or carrier.

An additional aspect of the present invention is a method for improving the health of a subject with breast cancer having one or more side effects associated with an aromatase inhibitor such as third generation aromatase inhibitor therapy comprising administering a pharmaceutical comprising an effective amount of an androgenic agent, and, optionally, a pharmaceutically acceptable excipient and/or carrier; or an effective amount of an androgenic agent, an effective amount of a third generation aromatase inhibitor, and, optionally, a pharmaceutically acceptable excipient and/or carrier.

BRIEF DESCRIPTION OF THE DRAWINGS

The foregoing aspects and advantages of the present invention will be readily apparent to one skilled in the art upon reference to the figures and the detailed description which follows.

FIG. 8 is a questionnaire of the endocrine subscale for the FACT-B.

DETAILED DESCRIPTION OF THE PREFERRED EMBODIMENTS

Definitions

Figure 1:
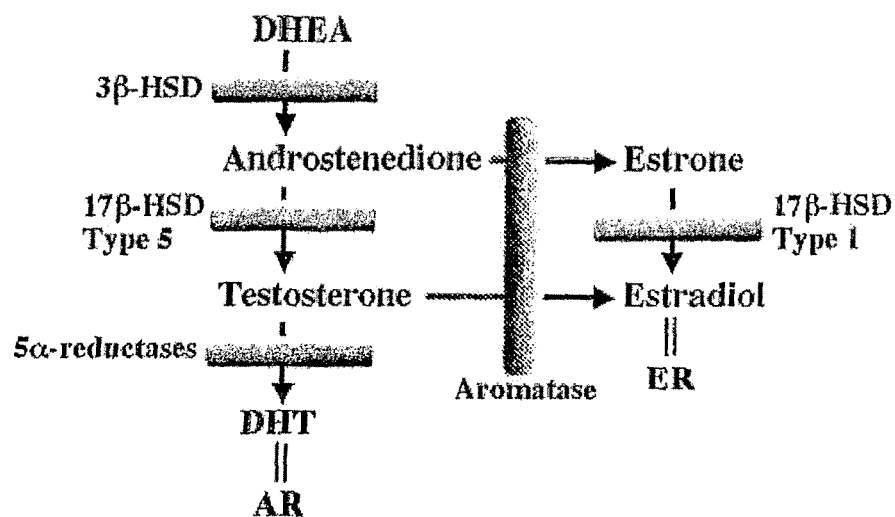
FIG. 1 is a schematic diagram depicting various biological steroid reaction pathways.

Terms are used herein as generally used in the art, unless otherwise defined in the following:

The term "a" or "an" refers to one or more of the described entity; for example, "an aromatase inhibitor" is understood to represent one or more aromatase inhibitors. Another example is "an androgenic agent" is understood to represent one or more androgenic agents. Another example is "for improving a side effect" is understood to include improving one or more side effects. As such, the terms "a" (or "an"), "one or more," and "at least one" can be used interchangeably herein.

The term "about" as used herein may be applied to modify any quantitative representation that could permissively vary without resulting in a change in the basic function to which it is related.

"Adjuvant therapy" may include adjuvant, neo-adjuvant and/or palliative therapy.

"Androgenic agent" refers to a chemical that increases androgenic activity or synthesis. Typically, an androgenic agent is a steroid hormone that binds with high affinity (in the pM or nM range) and specificity to its intracellular mediator, the androgen receptor, to stimulate transactivation activity and thus regulate the expression of target genes. Examples are provided herein.

"Aromatase inhibitor" refers to a chemical compound or polypeptide that blocks or inhibits the activity of aromatase which is an enzyme that converts androgens to estrogens. Examples are provided herein.

"Breast cancer" refers to a malignant proliferation of epithelial cells lining the ducts or lobules of the breast.

"Collagen crosslink" refers to a pyridinoline and deoxypyridinoline crosslink.

"Diagnosed" is meant to include a subject suspected or predicted to have breast cancer.

"Effective amount" or "pharmaceutically effective amount" of an agent or compound as provided herein refers to a nontoxic but sufficient amount of the agent or compound to provide the desired therapeutic effect. As will be pointed out below, the exact amount required will vary from subject to subject, depending on age, general condition of the subject, the severity of the condition being treated, and the particular agent or compound administered, and the like. An appropriate "effective amount" in any individual case may be determined by one of ordinary skill in the art by reference to the pertinent texts and literature and/or using routine experimentation.

"Improving one or more side effects" includes, but is not limited to, the prevention, treatment, reversal, part-reversal, reduction, diminution, or amelioration of a side effect.

"Improving the health of a subject" includes, but is not limited to, improving one or more side effects and/or improving the therapeutic effect of the aromatase inhibitor.

"Pharmaceutically acceptable" refers to those compounds, agents, materials, compositions, excipients, and/or dosage forms that are, within the scope of sound medical judgment, suitable for contact with the tissues of human beings and animals without excessive toxicity, irritation, allergic response, or other problems or complications commensurate with a reasonable benefit/risk ratio.

"Post-menopausal woman" is defined to include not only a woman of advanced age who has passed through menopause, but also a woman who has been hysterectomized or for some other reason has suppressed estrogen production, such as one who has undergone long-term administration of corticosteroids, suffer from Cushions' syndrome or have gonadal dysgenesis.

"Side effect" refers to a consequence other than the one(s) for which an agent or measure is used, as the adverse effects produced by a drug, especially on a tissue or organ system other then the one sought to be benefited by its administration. Examples are providing herein.

"Subject" is an animal including the human species that is treatable with the compositions, methods and kits of the present invention. The term "subject" or "subjects" is intended to refer to both the male and female gender unless one gender is specifically indicated.

The term "treatment" or "therapy" as used herein includes preventative (e.g., prophylactic) and palliative treatment and "treating" as used herein refers to the act of providing preventative and/or palliative treatment.

It will be apparent to one skilled in the art, in view of the following detailed description and the claims appended hereto, that various substitutions and/or modifications may be made to the present invention without departing from the scope of the invention as claimed.

Pharmaceutical Compositions

A pharmaceutical composition for improving one or more side effects associated with aromatase Inhibitor treatment in a subject with breast cancer, comprising (a) an effective amount of androgenic agent, and optionally (b) a pharmaceutically acceptable excipient and/or carrier is within the scope of the present invention. Furthermore, a pharmaceutical composition for improving one or more side effects associated with aromatase inhibitor treatment in a subject with breast cancer comprising (a) an effective amount of androgenic agent, (b) an effective amount of an aromatase inhibitor, and optionally (c) a pharmaceutically acceptable excipient and/or carrier is within the scope of the present invention.

An androgenic agent of the present invention can, for example, be selected from the group consisting of: testosterone, methyl testosterone, testosterone undecanoate, testosterone propionatedihydrotestosterone, 5α-dihydrotestosterone, or alternatively androstenediol androstenediol-3-acetate, androstenediol-17-acetate, androstenediol-3,17-diacetate, androstenediol-17-benzoate, androstenediol-3-acetate-17-benzoate, androstenedione, adrenosterone, androsterone acetate, androsterone propionate, androsterone benzoate, dehydroepiandrosterone, sodium dehydroepiandrosterone sulfate, oxymetholone, fluoxymesterone, methandrostenolone, testolactone, pregnenolone, 17α-methylnortestosterone, norethandrolone, dromostanolone, dromostanolone propionate, nandrolone, nandrolone phenpropionate, nandrolone decanoate, nandrolone furylpropionate, nandrolone cyclohexanepropionate, nandrolone benzoate, nandrolone cyclohexanecarboxylate, danazol, oxymetholone, androsterone, stanozolol, ethylestrenol, oxandrolone, bolasterone, mesterolone, testosterone cypionate, testosterone phenylacetate, testosterone enanthate, testosterone acetate, testosterone buciclate, testosterone heptanoate, testosterone decanoate, testosterone caprate, testosterone isocaprate, and isomers, metabolites, derivatives, and precursors of any of the aforementioned compounds, and combinations thereof. In addition to the pharmaceutically acceptable esters of testosterone, esters of dihydrotestosterone, include, but are not limited to, the enanthate, propionate, cypionate, phenylacetate, acetate, isobutyrate, buciclate, heptanoate, decanoate, undecanoate, caprate and isocaprate esters. The aforementioned esters are commercially available or may be readily prepared using techniques known to those skilled in the art or described in the pertinent literature.

The aforementioned androgenic agents are selected from the group consisting of naturally occurring androgens, synthetic androgens, metabolites, precursors, and derivatives thereof. The agents may be incorporated into the present dosage units and thus administered in the form of a pharmaceutically acceptable derivative, metabolite, precursor, analog, ester, salt, or amide, or the agents may be modified by appending one or more appropriate functionalities to enhance selected biological properties such as penetration through mucosal tissue. In general, with regard to androgenic agents, esters are preferred relative to salts or other derivatives.

Preparation of esters, as noted in the preceding section, involves functionalization of hydroxyl and/or carboxyl groups that may be present, as will be appreciated by those skilled in the arts of pharmaceutical chemistry and drug delivery. For example, to prepare testosterone esters, the 17-hydroxyl group of the testosterone molecule is generally caused to react with a suitable organic acid under esterifying conditions, such conditions typically involving the use of a strong acid such as sulfuric acid, hydrochloric acid, or the like, and a temperature sufficient to allow the reaction to proceed at reflux. Esters can be reconverted to the free acids, if desired, by using conventional hydrogenolysis or hydrolysis procedures.

Preferably, the androgenic agent of the present invention is testosterone, methyltestosterone, testosterone undecanoate, testosterone propionate, dehydroepiandrosterone, or sodium dehydroepiandrosterone sulfate, or a metabolic precursor, metabolite, or derivative thereof. More preferably, the androgenic agent of the present invention is testosterone, methyltestosterone, testosterone undecanoate, or testosterone propionate, or a metabolic precursor, metabolite, or derivative thereof. Most preferably, the androgenic agent is provided in the form of testosterone undecanoate, an orally active testosterone preparation that is a fatty acid ester of the natural androgen testosterone. Unlike other oral testosterone preparations, testosterone undecanoate is able to by-pass the liver via the lymphatic system and is therefore orally bioavailable.

Additionally, testosterone is difficult to deliver orally, as 80-90% is broken down in the liver as it is absorbed from the gut. As such, alternate delivery mechanisms have been explored, e.g. the aforementioned testosterone patch (Intrinsa®) by Proctor & Gamble used to improve sexual libido in post-menopausal women because of the progressive decline in testosterone levels with age and in women who have their ovaries removed.

An effective amount of an androgenic agent may vary among each androgenic agent. For example, an effective amount per day of testosterone may vary. In one embodiment, an effective amount of testosterone may be between about 2 to about 80 mg, between about 5 to about 75 mg, between about 10 to about 70 mg, between about 20 to about 60 mg, between about 30 to about 50 mg, and between about 35 to about 45 mg. In another embodiment, a preferred amount is about 20 mg. In one embodiment, a preferred amount is about 40 mg. In one embodiment, a preferred amount is about 50 mg.

An effective amount per day of methyltestosterone may vary. In one embodiment, an effective amount of methyltestosterone may be between about 0.1 mg to about 10 mg, between about 0.5 mg to about 9 mg, between about 1 mg to about 9 mg, between about 2 mg to about 8 mg, between about 3 mg to about 7 mg, and between about 4 mg to 5 mg. In one embodiment, a preferred amount is about 0.5 mg. In another embodiment, a preferred amount is about 1.25 mg. In one embodiment, a preferred amount is about 2.5 mg.

An effective amount per day of testosterone undecanoate may vary. In some embodiments, an effective amount of testosterone undecanoate may be between about 10 to about 120 mg, between about 20 to about 110 mg, between about 30 to about 100 mg, between about 40 to about 90 mg, between about 50 to about 80 mg, and between about 60 to about 70 mg. In one embodiment, a preferred amount is about 20 mg. In another embodiment, a preferred amount is about 40 mg. In one embodiment, a preferred amount is about 80 mg.

An effective amount per day of testosterone propionate may vary. In some embodiments, an effective amount of testosterone propionate may be between about 10 to about 120 mg, between about 20 to about 110 mg, between about 30 to about 100 mg, between about 40 to about 90 mg, between about 50 to about 80 mg, and between about 60 to about 70 mg. In one embodiment, a preferred amount is about 20 mg. In another embodiment, a preferred amount is about 40 mg. In one embodiment, a preferred amount is about 80 mg.

The effective amount of androgenic agent used in conjunction with an aromatase inhibitor is relatively lower than a standard dose because of low levels of sex hormone binding globulin which may be caused by the aromatase inhibitor.

Sex hormone binding globulin binds an androgenic agent (e.g., testosterone) and transports it around the body. Its production is regulated by several mechanisms, but one of the most profound effectors of its level is the amount of estrogen in the serum: the higher the estrogen, the higher the sex hormone binding globulin and the lower the free androgenic agent. Conversely, the lower the estrogen, the lower the sex hormone binding globulin, and the higher the free androgenic agent, which means the androgenic agent is has higher bioavailability. Thus after menopause, as the estrogen level falls, the sex hormone binding globulin level falls and the free androgenic agent such as testosterone rises. This free androgenic agent has multiple functions, as the androgen receptor is expressed in all cells of the body.

In some instances, dosage levels below the lower limit of the aforesaid range may be more than adequate, while in other cases still larger doses above the upper limit of the aforesaid range may be employed without causing any harmful side effects.

An aromatase inhibitor of the present invention, for example, can be selected from the group consisting of either steroidal or nonsteroidal aromatase inhibitors, and/or isomers thereof. Steroidal aromatase inhibitors developed to date build upon the basic androstenedione nucleus and incorporate chemical substituents at varying positions on the steroid. Examples of steroidal aromatase inhibitors include, but are not limited to, exemestane (Aromasin®) and formestane. Additional examples include mechanism-based steroidal aromatase inhibitors that mimic the substrate, are converted by the enzyme to a reactive intermediate, and result in the inactivation of aromatase. Preferably, an aromatase inhibitor of the present invention is exemestane.

Nonsteroidal aromatase inhibitors can be divided into three classes: aminoglutethimide-like molecules, imidazole/triazole derivatives, and flavonoid analogs. Examples of non-steroidal aromatase inhibitors include, but are not limited to, anastrozole (Arimidex®), letrozole (Femara®), vorozole and fadrozole. Preferably, an aromatase inhibitor of the present invention is either anastrozole or letrozole.

Aromatase inhibitors often include third-generation aromatase inhibitors, such as anastrozole (Arimidex®), exemestane (Aromasin®), and letrozole (Femara®). These third generation aromatase inhibitors have brought about a major change in the therapeutic approach to patients with hormone-sensitive breast cancer. Such aromatase inhibitors are very specific in their action in that they virtually ablate estrogen in the serum and thus lower sex hormone binding globulin, which enables the achievement of a synergistic effect in embodiments of the invention.

An effective amount of an aromatase inhibitor may vary among each aromatase inhibitor. For example, an effective amount per day for Aromasin® may vary. In some embodiments, an effective amount may be between about 5 to about 100 mg, between about 10 to about 80 mg, between about 20 to about 70 mg, between about 30 to about 60 mg, and between about 40 to about 50 mg. Also, in some embodiments, an effective amount may be between about 25 to about 100 mg and between about 35 to about 100 mg. Furthermore, in some embodiments, an effective amount may be between about 25 to about 150 mg, about 50 to about 150 mg, and about 80 to about 150 mg. In one embodiment, a preferred amount is about 25 mg.

An effective amount per day of Arimidex® may vary. In some embodiments, an effective amount for Arimidex® may be between about 0.1 mg to about 5 mg, between about 0.5 mg to about 4 mg, between about 1 mg to about 3 mg, and between about 1.5 mg to about 2.5 mg. Also, in some embodiments, an effective amount may be between about 1 mg to about 5 mg and between about 1.5 mg to about 5 mg. Furthermore, in some embodiments, an effective amount may be between about 1 mg to about 7.5 mg, between about 1 mg to about 10 mg, and between about 1 mg to about 20 mg. In one embodiment, a preferred amount is about 1 mg.

An effective amount per day of Femara® may vary. In some embodiments, an effective amount may be between about 1 to about 5 mg, between about 1.5 to 4 mg, between about 2 to about 3.5 mg, and between about 2.5 to about 3 mg. Also, in some embodiments, an effective amount may be between about 2.5 mg to about 5 mg and between about 3.5 mg to about 5 mg. Furthermore, in some embodiments, an effective amount may be between about 2.5 mg to about 7.5 mg, between about 2.5 mg to about 10 mg, and between about 2.5 mg to about 20 mg. In one embodiment, a preferred amount is about 2.5 mg.

In some instances, dosage levels below the lower limit of the aforesaid range may be more than adequate, while in other cases still larger doses above the upper limit of the aforesaid range may be employed without causing any harmful side effects. For example, dosages of an aromatase inhibitor above the upper limit may be used to improve the bioavailability of an androgenic agent such as testosterone or dihydrotestosterone, as described below.

Testosterone naturally is not highly absorbed because it is broken down approximately 85% in the intestines by aromatase and other metabolic pathways into by-products such as inactive testosterone and dihydrotestosterone. The administration of an aromatase inhibitor in combination with testosterone, however, results in an increased absorption, and subsequently greater bioavailability.

In one embodiment of the invention, the administration of an aromatase inhibitor in combination with testosterone results in an improvement in the bioavailability of testosterone between about 10% to about 50%, between about 20% to about 40%, and between about 25% to about 35%. A preferred amount of increase in bioavailability is greater than about 15%, greater than about 25%, greater than about 30%, or greater than about 35%.

In another embodiment of the invention, the administration of aromatase inhibitor in combination with testosterone results in an improvement in the bioavailability of dihydrotestosterone between about 25% to about 75%, between 35% to about 65%, and between 45% to 55%. A preferred amount of increase in dihydrotestosterone bioavailability is greater than about 25%, greater than about 35%, greater than about 45, or greater than about 55%.

An embodiment of the invention includes a pharmaceutical composition comprising an androgenic agent and an aromatase inhibitor. A preferred embodiment is a pharmaceutical composition comprising a testosterone. A specific embodiment consists of testosterone undecanoate. An additional embodiment consists of about 40 mg of testosterone undecanoate.

Another embodiment of the invention includes a pharmaceutical composition comprising an androgenic agent and an aromatase inhibitor selected from the group consisting of exemestane, formestane, anastrozole, letrozole, vorozole, or fadrozole. A preferred embodiment consists of anastrozole. A specific embodiment consists of about 1 mg of anastrozole.

A specific embodiment taught by the invention consists of a pharmaceutical composition comprising testosterone undecanoate and anastrozole. More specifically, this embodiment comprises about 40 mg of testosterone undecanoate and about 1 mg of anastrozole.

An alternative embodiment of the invention includes a pharmaceutical composition comprising an androgenic agent.

An alternative embodiment of the invention includes a pharmaceutical composition comprising an androgenic agent linked to an aromatase inhibitor, e.g., via an ester linkage.

Another alternative embodiment of the invention includes a pharmaceutical composition comprising an androgenic agent/aromatase inhibitor complex, wherein the complex is created by known methods in the art.

Methods of Administering the Pharmaceutical Compositions of the Present Invention A method of administering a pharmaceutical composition of the present invention to improve one or more side effects associated with aromatase inhibitor treatment in a subject with breast cancer is within the scope of the present invention.

Pharmaceutical compositions of this invention can be administered by any route compatible with a desired outcome. Thus, routes of administration include orally (e.g., ingestion or inhalation), intraperitoneally, intradermally, transdermally, transmucosally, subcutaneously, sublingually, intravenously, intraarterially, intracavity, intracranially, intramuscularly, parenterally, or topically. Preferably, the aromatase inhibitor and the androgenic agent are administered orally or transdermally.

The pharmaceutically acceptable agents are administered alone or in combination with pharmaceutically acceptable carriers, excipients, or diluents, and such administration may be carried out in single or multiple doses. More particularly, the therapeutic agents of this invention can be administered in a wide variety of different dosage forms, i.e., they may be combined with various pharmaceutically acceptable inert carriers or excipients in the form of tablets, capsules, emulsions, lozenges, troches, hard candies, lollipops, powders, sprays, creams, salves, suppositories, jellies, gels, pastes, lotions, ointments, aqueous suspensions, injectable solutions, elixirs, syrups, injectable depots, implants, microencapsulated delivery systems, oil-based suspensions, and the like.

For example, androgenic agents may be administered by the aforementioned routes and dosage forms. In one embodiment, testosterone esters may be injected. These may include testosterone enanthate (Delatestryl) which is suspended in sesame oil, testosterone cypionate (Depo-Testosterone) which is suspended in cottonseed oil, testosterone propionate (Testovis; Virormone), testosterone phenylpropionate (Testolent), and a blend of four testosterone esters (Sustanon; Omnadren) which include testosterone propionate, testosterone phenylpropionate, testosterone isocaproate, and testosterone decanoate.

In another embodiment, testosterone may be injected as an aqueous suspension (Aquaviron).

In another embodiment, testosterone may be administered via a transdermal patch (Androderm; Testoderm TTS).

In another embodiment, testosterone may be administered by a gel (Androgel; Testim).

In another embodiment, methyltestosterone may be administered orally, e.g., tablet. (Metesto, Methitest, Testred, Oreton Methyl, and Android).

In another embodiment, testosterone undecanoate may be administered orally, e.g., tablet (Androxon, Understor, Restandol, and Restinsol).

In one embodiment, testosterone may be administered buccally (Striant).

In another embodiment, testosterone may be administered subcutaneously, e.g., pellet (Testopel).

The instant pharmaceutical combinations comprising an aromatase inhibitor of the invention in combination with an androgenic agent include administration of a single pharmaceutical dosage formulation which contains both substances, as well as administration of each agent in its own separate pharmaceutical dosage formulation.

It is well known that patient compliance is a factor in receiving a good result in medical treatment. Causes for poor compliance may include, but are not limited to, complicated regimen, unattractive and/or painful formulation such as needles, and physical difficulty in complying. Therefore, administration of two or even more different dosage forms to the patient may not be convenient or satisfactory to achieve the most optimal results. A pharmaceutical composition of the present invention comprising an androgenic agent and aromatase inhibitor combined into a single dosage form may provide improved patient compliance.

Where separate dosage formulations are used, the aromatase inhibitor and the androgenic agent can be administered at essentially the same time, i.e., concurrently, or at separately staggered times. i.e., sequentially. The pharmaceutical compositions of the present invention is understood to include all these regimens. Administration of the pharmaceutical composition by any routes mentioned above using any of these regimens is suitable for the present invention as long as the beneficial pharmaceutical effect of the aromatase inhibitor and androgenic agent are realized by the patient. It is preferred that the aromatase inhibitor and androgenic agent be administered concurrently on a once-a-day dosing schedule; however, varying dosing schedules, such as the aromatase inhibitor once per day and the androgenic agent once, twice or more times per day, or the androgenic agent once per day and the aromatase inhibitor once, twice or more times per day, is also encompassed herein. A single oral daily dosage formulation comprised of both the aromatase inhibitor and androgenic agent is preferred. A single dosage formulation will provide convenience for the subject.

The appropriate dosing regimen utilizing the pharmaceutical compositions, the amount of each dose administered, and the intervals between doses of the compounds according to the present invention will depend on various factors such as the particular aromatase inhibitor and androgenic agent being used in combination, the type of pharmaceutical formulation being used, the type of physiological condition being treated, the characteristics of the subject being treated (e.g., species, age, weight, sex, medical condition, fed/fasted), the route of administration, and the severity of the disorder being treated. A physician or veterinarian of ordinary skill can readily determine and prescribed the effective amount of the pharmaceutical composition to prevent or to treat the specific physiological condition.

Such compositions may be administered in a single daily dose, or the total daily dosage may be administered in divided doses several times daily. Furthermore, the pharmaceutical compositions may be administered as a single dose or over a period of time. Additionally, the pharmaceutical composition can be administered continuously or intermittently. The daily dosage may be varied over wide range and can be such that the amount of the active compound selected from the androgenic agent and/or aromatase inhibitor is sufficient to cause its desired effects.

The pharmaceutical compositions of the present invention are administered to a subject diagnosed with breast cancer, preferably a perimenopausal or a postmenopausal woman.

The duration of treatment for administration of the pharmaceutical compositions of the present invention may vary between about three months to about ten years, between about four months to about five years, and between about six months to about four years. A preferred duration of treatment is about six months. Another preferred duration of treatment is about five years.

The composition or formulation to be administered will contain a quantity of the compounds or pharmaceutically acceptable salts thereof of the invention in an amount effective to treat the disease/condition of the subject being treated. Because two different compounds are being used together in a combination therapy, the potency of each of the compounds and the interactive effects achieved by combining them together must also be taken into account. A consideration of these factors is well within the purview of the ordinarily skilled clinician for the purpose of determining the therapeutically effective or prophylactically effective dosage amounts needed to improve side effects.

Administration of the pharmaceutical composition to the subject includes both self-administration and administration to the subject by another person (e.g., physician, health care worker, friend).

An embodiment of the present invention includes a method for improving one or more side effects associated with aromatase inhibitor treatment in a subject diagnosed with breast cancer comprising administering a pharmaceutical composition, as described previously, to a subject orally or transdermally. A specific embodiment includes a method of administering a solid oral dosage form (e.g., tablet) once a day.

Another embodiment of the present invention involves a method of administering pharmaceutical compositions, described above, as adjuvant, neo-adjuvant or palliative therapy to a subject with breast cancer who has already received chemotherapy.

An additional embodiment of the present invention involves a method of increasing the absorption rate of an androgenic agent in a subject diagnosed with breast cancer comprising administering pharmaceutical compositions described within the specification. A specific embodiment of the present invention includes increasing the absorption rate of testosterone orally if conversion of estrogen is blocked in small bowel mucosa, submucosa, microvessels, lymphatics and liver by an aromatase inhibitor. As aromatase is a major enzyme in the small bowel and liver, specific high efficiency aromatase inhibitors will reduce testosterone metabolism on oral intake.

Measuring Side Effects Associated with Aromatase Inhibitor Treatment

A method for measuring side effects associated with aromatase inhibitor treatment is within the scope of the present invention.

Both steroidal and non-steroidal aromatase inhibitors have shown clinical efficacy in the treatment of breast cancer. Recently, the American Society of Oncology has recommended that aromatase inhibitor be used as adjuvant therapy in all post-menopausal women with hormonally sensitive early breast cancer. This raises significant problems with the management of side-effects caused by total estrogen deprivation for periods of between five and ten years. Currently, the duration of hormonal adjuvant therapy is five years. However, this concept is being challenged, which may result in a longer duration of estrogen deprivation (Baum 2005). Most of the side-effects of aromatase inhibitors can be attributed to estrogen deprivation in specific tissues, but some are difficult to categorize. An example is loss of libido, which may have several synergistic etiologies, but appears to be significantly higher in Al than in TAM usage (Fallowfield, Cella et al 2004). However, there is little doubt that the musculoskeletal side-effects, such as arthralgia and osteoporosis, are a direct result of estrogen deprivation in these tissues and are a frequent occurrence in aromatase inhibitor users (Ingle 2005). Bone fractures during aromatase inhibitor therapy may be increased by as much as 60%, and this is probably a result of increased bone turnover (up by 20%), as well as accelerated bone loss (Eastell and Hannon 2005). The long-term side-effects of aromatase inhibitors are not known but are of concern, especially in the area of cognition (Jenkins. Shilling et al 2004), where estrogen is known to be especially important (reviewed in Sherwin 2003). There appears to be a critical window in the perimenopausal period in which hormone levels may be critical to cognitive function (Sherwin 2003).

Administration of an androgenic agent simultaneously in combination with an aromatase inhibitor or following the administration of an aromatase inhibitor serves to improve one or more side effects associated with aromatase inhibitor administration, such as hot flush, hot flash, vasodilatation, osteoporosis, osteopenia, loss of libido, weight gain, vaginal dryness, sleeping difficulties, night sweats, asthenia, painful intercourse, pain, whole body pain, arthritis, arthralgia, breast pain, pharyngitis, depression, bloating, nausea, rash, mood swings, headache, diminished cognitive function, hypertension, insomnia, lymphoedema, back pain, peripheral edema, cold sweats, abdominal pain, injury, constipation, coughing, diarrhea, fracture, hypercholesteremia, dyslipidemia, infection, arthrosis, dizziness, dyspnea, paraesthesia, urinary tract infection, vulvovaginitis, anxiety, bone pain, chest pain, dyspepsia, flu syndrome, gastrointestinal disorder, sweating and/or leukorrhea. Preferably, administration of an androgenic agent simultaneously in combination with an aromatase inhibitor or following the administration of an aromatase inhibitor serves to improve one or more side effects associated with aromatase inhibitor administration, such as hot flush, hot flash, vasodilatation, osteoporosis, osteopenia, night sweats, whole body pain, arthritis, arthralgia, pain, diminished cognitive function, and arthrosis.

One embodiment of the present invention involves measuring serum, urine, and/or fecal levels of markers for bone resorption. Such markers of bone resorption include, but are not limited to, carboxy-terminal collagen crosslinks (pyridinoline, deoxypryridinoline) N-telopeptide, hydroxyproline, tartrate-resistant acid phosphatases, and galactosyl hydroxylysine. Also, markers for bone formation such as osteocalcin may be measured. Another measurement of bone resorption/bone formation are changes in calcium and phosphorus balances (positive or negative) which are determined by measuring the difference between the total excretion (feces and urine) and the dietary intake of calcium or phosphorus ion. (These balances are positive when the total excretion is less than the dietary intake.) Preferably, serum levels of carboxy-terminal crosslinks are measured.

Another embodiment of the present invention involves measuring the quality of life caused by estrogen deprivation. There are endocrine therapies for use with women who have breast cancer. Several clinical trials of adjuvant therapy comparing different drugs with the aim of determining efficacy, toxicity and overall general health and well-being are in progress or have recently reported. Publications containing the systematic collection of comprehensive subjective data to date are few thus little is known about the impact that hormone therapy exert on the quality of women's lives. The side-effects of some endocrine therapies may be underestimated by healthcare professionals when their views are compared with those of patients. However the side-effects of different treatments and the impact that these may have on quality of life (QOL) must be determined if informed choices about disease management are to be made. For example, menopausal symptoms may be considered too high a price for some women to pay in adjuvant therapy, especially if such treatment is still of unknown benefit in terms of preventing recurrence of the disease. Furthermore, without an assessment of quality of life, it is difficult to know what supportive and ameliorative interventions may be needed to accompany the treatment found to be most efficacious in terms of treating breast cancer and preventing its recurrence. The magnitude of difference between treatment groups that may be expected in terms of QOL and the incidence of symptoms is likely to be larger than the differences in survival.

There are several quality of life instruments or assessments that can used to assess the impact that hormone treatment (and the inventions disclosed herein) have on different aspects of a person's functioning and well being. Other ways of measuring or assessing the side effects associated with the inventions disclosed herein are available and will be known to those of skilled in the art and, if appropriate, may be used.

An endocrine subscale (FACT-ES) to accompany a well-validated QOL measure called the FACT-B (Brady, M J., et al., Journal of Clinical, Oncology., Vol. 15, No. 3 (March 1997) pp. 974-986, which is incorporated in its entirety) was developed specifically for use in trials using drugs likely to cause endocrine related symptoms. See Fallowfield, L J, et al., Breast Cancer Research and Treatment. Vol. 55, No. 2, 1999, pp. 189-199, which is incorporated herein by reference in its entirety. Also, FACT-ES is a validated questionnaire designed to measure quality of life of women with breast cancer who are being treated with endocrine therapies. It consists of the FACT-B questionnaire plus an additional endocrine subscale. FACT-B (breast) consists of the FACT-G (general) QOL tool for cancer patients plus the Breast Cancer subscale. FACT-ES has been developed to measure QOL in patients receiving endocrine therapy for breast cancer. This instrument (FACT-ES) should, therefore, be sensitive to QOL changes in patients in this trial. The FACT-B (version 4) is a multi-dimensional self-report questionnaire measuring five domains: physical well-being, social well-being, emotional well-being, functional well-being, and breast cancer concerns. It has good psychometric properties, discriminates well between groups and is responsive to change. It is relatively simple and quick to complete, has been translated into many different languages and is being used in a large number of breast trials in the US and Europe. This sub-protocol will assess the QOL in all consenting patients over this period and at recurrence, should this occur within the study period.

Another preferred embodiment of the present invention involves measuring joint pain using the visual numeric scoring (VNS) on the American College of Rheumatology scoring system. The Western Ontario and McMaster Universities (WOMAC) Osteoarthritis Index™ consists of three VAS, one each pertaining to pain, joint stiffness and physical function. This then gives the WOMAC™ osteoarthritis index composite score. (See Bellamy N. J Rheum 15:1833-1840, 1988, incorporated herein by reference in its entirety).

Another embodiment of this invention involves measuring cognitive function, including processing speed, working memory, visual memory, and verbal memory. The improvement of one or more side effects associated with aromatase inhibitor treatment in a subject diagnosed with breast cancer may be measured by the following (Fallowfied Assessment. (See Jenkins V. Psychooncology 13:61-66, 2004, incorporated herein by reference in its entirety).

A further embodiment of this invention involves measuring serum lipids, including, but not limited to, cholesterol. HDL, and LDL.

Manufacturing the Pharmaceutical Compositions of the Present Invention

A method for manufacturing a pharmaceutical composition of the present invention and any articles of manufacture produced thereof are within the scope of the present invention.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders. A lubricant may be necessary in a tablet formulation to prevent the tablet and punches from sticking in the die. The lubricant is chosen from such slippery solids as talc, magnesium and calcium stearate, stearic acid and hydrogenated vegetable oils. Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate. Also, super disintegrants including, but not limited to, Ac-Di-Sol® (sodium croscarmellose cellulose), Explotab® (sodium starch glycolate), VivaStar® (sodium starch glycolate), and Polyplasdone disintegrants may be used.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients. The size and shape of the tablet may vary according to standard dimensions and shapes known in the art.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders. The size and shape of the capsule may vary according to standard dimensions and shapes known in the art.

Furthermore, the capsule may be liquid-filled or non-liquid-filled. The capsule may be a hard or soft capsule. Furthermore, it may be a gelatin capsule, a starch capsule, a hydroxypropylmethylcellulose (HPMC) capsule, or a cellulosic capsule. Although not limited to capsules, such dosage forms can further be coated with, for example, a seal coating, an enteric coating, an extended release coating, or a targeted delayed release coating. Additionally, liquid-filled capsules of the present invention may be emulsions and/or may contain tocopherol as a carrier for poorly soluble compounds such as testosterone.

In one embodiment, the invention is directed to the use of tocopherol as the hydrophobic dispersed phase of emulsions containing water insoluble, poorly water soluble therapeutic agents, water soluble ones which have been modified to be less water soluble, or mixtures thereof. In a preferred embodiment alpha-tocopherol is employed. Alpha-tocopherol is secreted by the enterocytes into the lymphatics and is processed in a similar manner to other forms of vitamin E. Also called vitamin E, alpha-tocopherol is not a typical lipid oil. It has a higher polarity than most lipid oils, particularly triglycerides, and is not saponifiable. It has practically no solubility in water.

In an alternative embodiment, the invention is an alpha-tocopherol emulsion in the form of a self-emulsifying system where the system is to be used for the oral administration of water-Insoluble (or poorly water-soluble or water-soluble agents modified to be less water soluble or mixtures thereof) drugs where that is desired. In this embodiment, an oil phase with surfactant and drug or drug mixture is encapsulated into a soft or hard gelatin capsule. Suitable solidification agents with melting points in the range of 40 to 60° C., such as high molecular weight polyethylene glycols (MW>1000), and glycerides, such as those available under the trade name Gelucire (Gattefose Corp., Saint Priest, France), can be added to allow filling of the formulation into a hard gelatin capsule at a high temperature. Semi-solid formulations are formed upon room temperature equilibration. Upon dissolution of the gelatin in the stomach and duodenum, the oil is released and forms a fine emulsion with a mean droplet diameter of between about 1 to about 15 microns, between about 2 to about 10 microns, or between about 2 to about 5 microns spontaneously. The emulsion is then taken up by the microvilli of the intestine and released into the bloodstream.

In an alternative embodiment, the invention comprises microemulsions containing tocopherol, preferably alpha-tocopherol. Microemulsions refer to a sub-class of emulsions where the emulsion suspension is essentially clear and indefinitely stable by virtue of the extremely small size of the oil/drug microaggregates dispersed therein.

In another embodiment of the invention, PEGylated vitamin E (alpha-tocopheryl polyethylene glycol succinate, abbreviated TPGS) is used as a primary surfactant in emulsions of vitamin E. TPGS is utilized as a primary surfactant, a stabilizer and also as a supplementary solvent in emulsions of vitamin E. TPGS is a water-soluble derivative of d-alpha-tocopheryl succinate. It is also used as an absorption and bioavailability enhancer for certain water-insoluble drugs (e.g. the HIV protease inhibitor amprenavir) and fat-soluble vitamins such as vitamin D. TPGS, because of its amphipathic nature (has both hydrophilic and lipophilic ends), forms its own micelles and thus does not require bile salts to do so. This makes it an excellent alpha-tocopherol substance for those who have problems secreting bile salts into the intestine (e.g., those with chronic childhood cholestasis).

TPGS may enhance the absorption of lipophilic drugs if formulated together with them. For this reason, the HIV protease inhibitor amprenavir is formulated with TPGS. Further, the enhancement of the oral bioavailability of some drugs when co-administered with TPGS may, in part, be due to inhibition of P-glycoprotein in the intestine. P-glycoprotein is the multidrug resistance transporter and is involved in the mediation of multidrug resistance.

In addition, polyethylene glycol (PEG) is also useful as a co-solvent in the emulsions of this invention. Of particular use is polyethylene glycol 200, 300, 400 or mixtures thereof.

The alpha-tocopherol concentration of the emulsions of this invention can be between about 1 to about 10% w/v, between about 2 to about 5% w/v, or between about 3 to about 4% w/v. The ratio of alpha-tocopherol to TPGS is optimally between about 1:1 to about 10:1 (w/w), between about 1:1 to about 5:1 (w/w), or between about 1:1 to about 15:1 (w/w).

The emulsions of the invention may further include surfactants such as ascorbyl-6 palmitate, stearylamine. PEGylated phospholipids, sucrose fatty acid esters and various vitamin E derivatives comprising Q-tocopherol nicotinate, tocopherol phosphate, and nonionic, synthetic surfactant mixtures, such as polyoxypropylene-polyoxyethylene glycol nonionic block copolymer.

The emulsions of the invention can comprise an aqueous medium. The aqueous phase generally has an osmolality of approximately 300 mOsm and may include sodium chloride, sorbitol, mannitol, polyethylene glycol, propylene glycol albumin, polypep and mixtures thereof. Osmolality may also range between about 100 to about 500 mOsm and between about 200 to about 400 mOsm. This medium can also contain various additives to assist in stabilizing the emulsion or in rendering the formulation biocompatible. Acceptable additives include acidifying agents, alkalizing agents, antimicrobial preservatives, antioxidants, buffering agents, chelating agents, suspending and/or viscosity-increasing agents, and tonicity agents. Preferably, agents to control the pH, tonicity, and increase viscosity are included. Optimally, a tonicity of at least 250 mOsm is achieved with an agent which also increases viscosity, such as sorbitol or sucrose. Tonicity may also be of at least 300 mOsm, at least 400 mOsm, or at least 500 mOsm.

The emulsions of the invention for intravenous injection have a particle size (mean droplet diameter) of about 10 to about 500 nm, preferably about 10 to about 200 nm and most preferably about 10 to about 100 nm. For intravenous emulsions, the spleen and liver will eliminate particles greater than 500 nm in size through the RES.

An embodiment of the invention includes testosterone within a liquid-capsule emulsion system.

Aqueous suspensions and/or elixirs are prepared by combining the active ingredient with various sweetening or flavoring agents, coloring matter or dyes, and, if so desired, emulsifying and/or suspending agents as well, together with such diluents as water, ethanol, propylene glycol, glycerin and various like combinations thereof. The amount of suspension may vary according to standard volumes known in the art.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate. It is preferred to formulate duloxetine and duloxetine-containing combinations as enteric compositions, and even more preferred to formulate them as enteric pellets. The size and shape of such formulations may vary according to standard dimensions and shapes known in the art.

Transdermal patches may also be used. Transdermal administration significantly enhances patient compliance by alleviating the discomfort of needles and other dosage forms by providing a convenient dosage form for once or twice weekly application. Such administration also provides the benefit of having sustained blood levels of the drug being administered. Typically patches comprise a resinous composition in which the drugs will dissolve, or partially dissolve, which is held in contact with the skin by a film which protects the composition. Other, more complicated patch compositions are also in use, particularly those having a membrane pierced with innumerable pores through which the drugs are pumped by osmotic action. The size of the patch may vary according to sizes known in the art.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are also in wide use.

For parenteral, intradermal, intramuscular, or subcutaneous administration pharmaceutical compositions may include one of the following, or any combination thereof: a sterile diluent, such as water, saline solution, fixed oils, polyethylene glycols, glycerine, propylene glycol or other synthetic solvents; surfactants such as polysorbate 80, sodium lauryl sulfate, sorbitan monopalmitate; alcohols; suspending agent such as agar, bentonite, microcrystalline cellulose, sodium carboxymethylcellulose, hydroxypropyl methylcellulose, tragacanth, veegum; antibacterial agents such as benzyl alcohol or methyl parabens; antioxidants such as ascorbic acid or sodium bisulfite; chelating agents such as ethylenediaminetetraacetic acid; and buffers such as acetates, citrates or phosphates and agents for the adjustment of tonicity such as sodium chloride or dextrose.

Pharmaceutical compositions can also include carriers to protect the composition against rapid degradation or elimination from the body, such as a controlled release or sustained release or extended release formulation, including implants and microencapsulated delivery systems. For example, a time delay material such as glyceryl monostearate or glyceryl stearate alone, or in combination with a wax, may be employed. Also, pharmaceutical compositions can include excipients that modify gut metabolism.

Additional methods of preparing various pharmaceutical compositions with a certain amount of each active ingredient are known, or will be apparent in light of this disclosure, to those skilled in this art.

The present invention is also directed to articles of manufacture such as kits which include the active ingredients of the invention in suitable pharmaceutical compositions packaged for distribution. Kits of the invention can additionally include instructions for using the kit components in a method of the invention. Instructions can include instructions for practicing any of the methods of the invention described herein. Thus, for example, a kit can include an androgenic agent or an aromatase inhibitor in a pharmaceutical formulation in a container, pack, or dispenser together with instructions for administration to a human subject. Instructions may additionally include indications of a satisfactory clinical endpoint or any adverse symptoms that may occur, or any additional information required by the Food and Drug Administration for use in humans.

The instructions may be on "printed matter," e.g., on paper or cardboard within the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM, and hybrids of these such as magnetic/optical storage media.

Kits can additionally include a buffering agent, a preservative, or a stabilizing agent. Each component of the kit can be enclosed within an individual container and all of the various containers can be within a single package.

Since the present invention relates to treatment with a combination of the two active ingredients which may be administered separately, the invention also relates to combining separate pharmaceutical compositions in kit form. The kit includes two separate pharmaceutical compositions: an androgenic agent and an aromatase inhibitor. The kit includes a container for containing the separate compositions such as a divided bottle or a divided foil packet, however, the separate compositions may also be contained within a single, undivided container. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of a kit is a so-called blister pack. Blister packs are well known in the packaging industry and are being widely used for the packaging of pharmaceutical unit dosage forms (e.g., tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It is desirable to provide a memory aid on a card insert, e.g., in the form of numbers next to the tablets or capsules whereby the numbers correspond with the days of the regimen which the tablets or capsules so specified should be administered. Another example of such a memory aid is a calendar printed on the card. Other variations of memory aids will be readily apparent.

Packaging can be accomplished by any of a number of means utilized in the pharmaceutical industry. Examples of such packaging are: unit dose containers for dispensing liquid compositions enclosed in a box or container along with package inserts; plastic and/or foil wrappers holding solid ocular inserts which contain the active ingredients of the invention and which are enclosed in a box or container along with package inserts. Other modes of packaging would be readily apparent to one skilled in the pharmaceutical packaging arts.

The following example is included for purposes of illustration only and is not intended to limit the scope of the present invention, which is defined by the appended claims. All references cited in the Example are incorporated herein by reference in their entireties.

Example 1 (Working)

The following example demonstrates the advantages of administering to a subject diagnosed with breast cancer a pharmaceutical composition comprising an androgenic agent and an aromatase inhibitor.

Five post-menopausal women having similar patient sociodemographic characteristics and ranging in age from 49 years to 56 years (median age 54) were selected for study. Each woman had been diagnosed with node-negative estrogen receptor and PR (Progesterone Receptor) positive BCa (Breast cancer), with tumor sizes ranging from 1.9 cm to 2.3 cm (median tumor size of 2.1 cm) and selected post-surgery (e.g., mastectomy, lumpectomy, or quadrantectomy for primary breast cancer) and post-chemotherapy. None had been subjected to previous attempts at hormone replacement therapy.

Each woman selected was subjected to four weeks of aromatase inhibitor therapy (anastrozole 1 mg (ARIMIDEX®) orally as a tablet once a day), and thereafter to an additional eight weeks of the same aromatase inhibitor therapy in combination with the oral administration of 40 mg of testosterone undecanoate as a tablet once a day. During this study, side effects associated with aromatase inhibitor treatment were measured at three separate times: prior to the first week of aromatase inhibitor therapy, following the fourth week of aromatase inhibitor therapy but before administration of testosterone undecanoate was begun, and following the eighth week of combined aromatase inhibitor and androgen replacement therapy. Measures of side effects were as follows: serum hormone levels, serum markers for bone resorption, serum lipid levels (see Haper-Wynne, et. al., Cancer Epidemiology, Biomakers & Prevention, Vol. 11, pp 614-621, July 2002, which is incorporated in its entirety herein). FACT-ES side-effect profile evaluations, arthralgia (joint pain) evaluations, and cognitive function evaluations. Charts depicting the results for these six measures as recorded at each of the three times are presented as FIG. 2 through FIG. 7. All result are the mean of individual scores with the bars representing standard error. As described hereafter, the novel therapies according to the present invention from this study demonstrate that androgen replacement therapy alleviates many of the side-effects of and/or enhances the efficacy of aromatase inhibitor therapy in breast cancer treatment.

Figure 2:
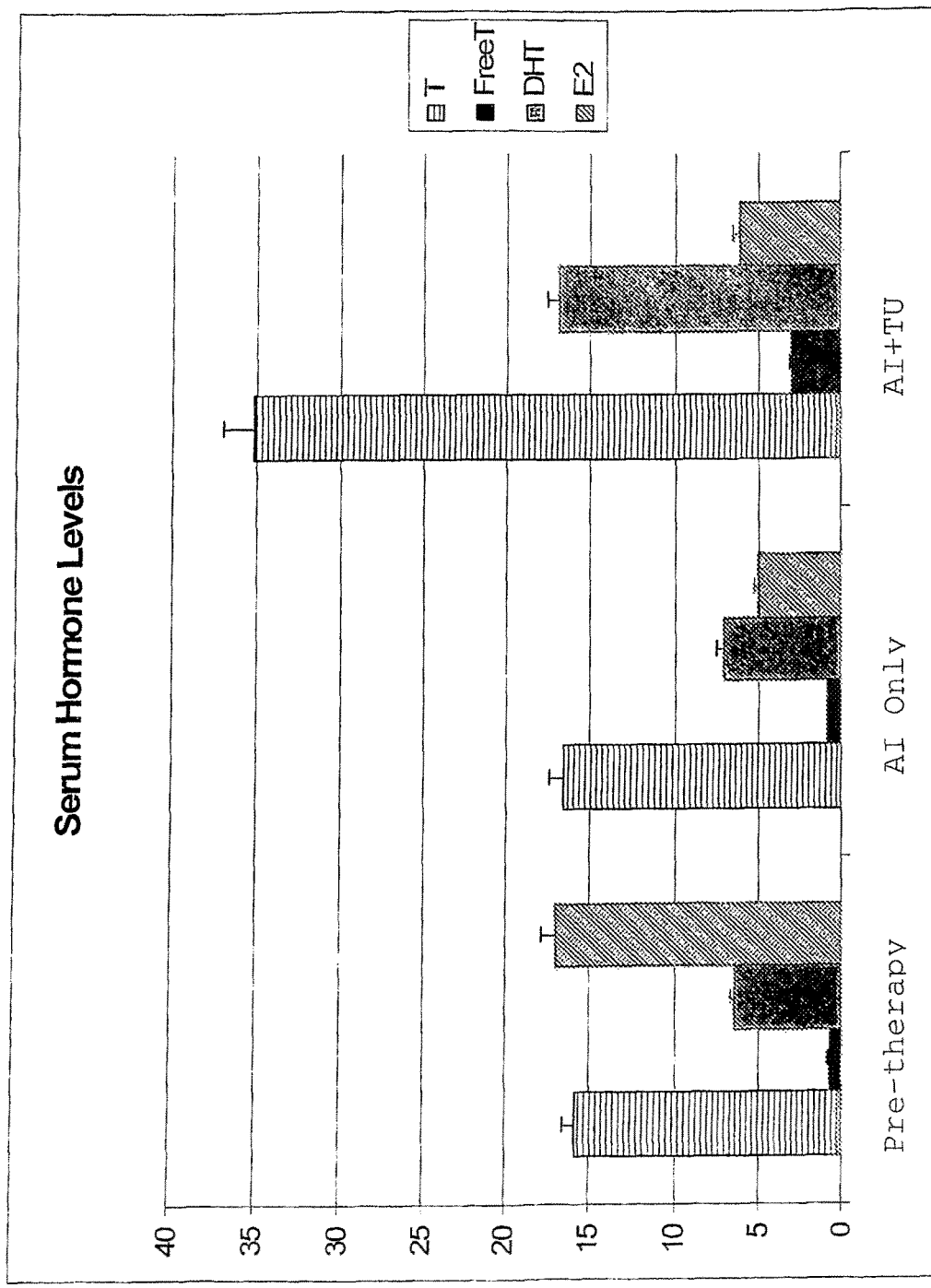
FIG. 2 is a chart demonstrating the effects of a combination of an aromatase inhibitor (Arimidex®) and an androgenic agent (testosterone undecanoate) upon serum hormone levels in post-menopausal patients referred to in the example described herein.

First, the chart in FIG. 2 demonstrates that testosterone aromatization to estradiol is almost completely ablated during aromatase inhibitor therapy, thus validating that the methods according to the present invention do not elevate levels of estrogen appreciably in a manner that could result in increased risk of relapse of breast cancer. The y axis is picomoles/L of serum. As depicted in FIG. 2, following the fourth week of aromatase inhibitor therapy (denoted by the "AI only" bars) the average estradiol (denoted by "E2" in the figure legend) serum level drops significantly from the average level prior to the beginning of aromatase inhibitor therapy (denoted "Pre-therapy"), while the remainder of the serum hormone levels appear relatively unchanged. After the subsequent eight weeks of combination aromatase inhibitor and androgen (testosterone undecanoate) replacement therapy (denoted "AI+TU"), there was only an insignificantly small increase in serum hormone levels of estradiol while levels of testosterone (denoted by "T" in the figure legend), free-testosterone (denoted by "FreeT" in the figure legend) and, in particular, dihydrotestosterone (denoted by "DHT" in the figure legend) have shown notable increases.

Applicants believe that this increase in DHT is the cause of improved patient well being and health as described hereafter with reference to FIG. 3 through FIG. 6, as increases in tissue-specific DHT levels will result in a reduction in the side-effects associated with aromatase inhibitors.

Figure 3:
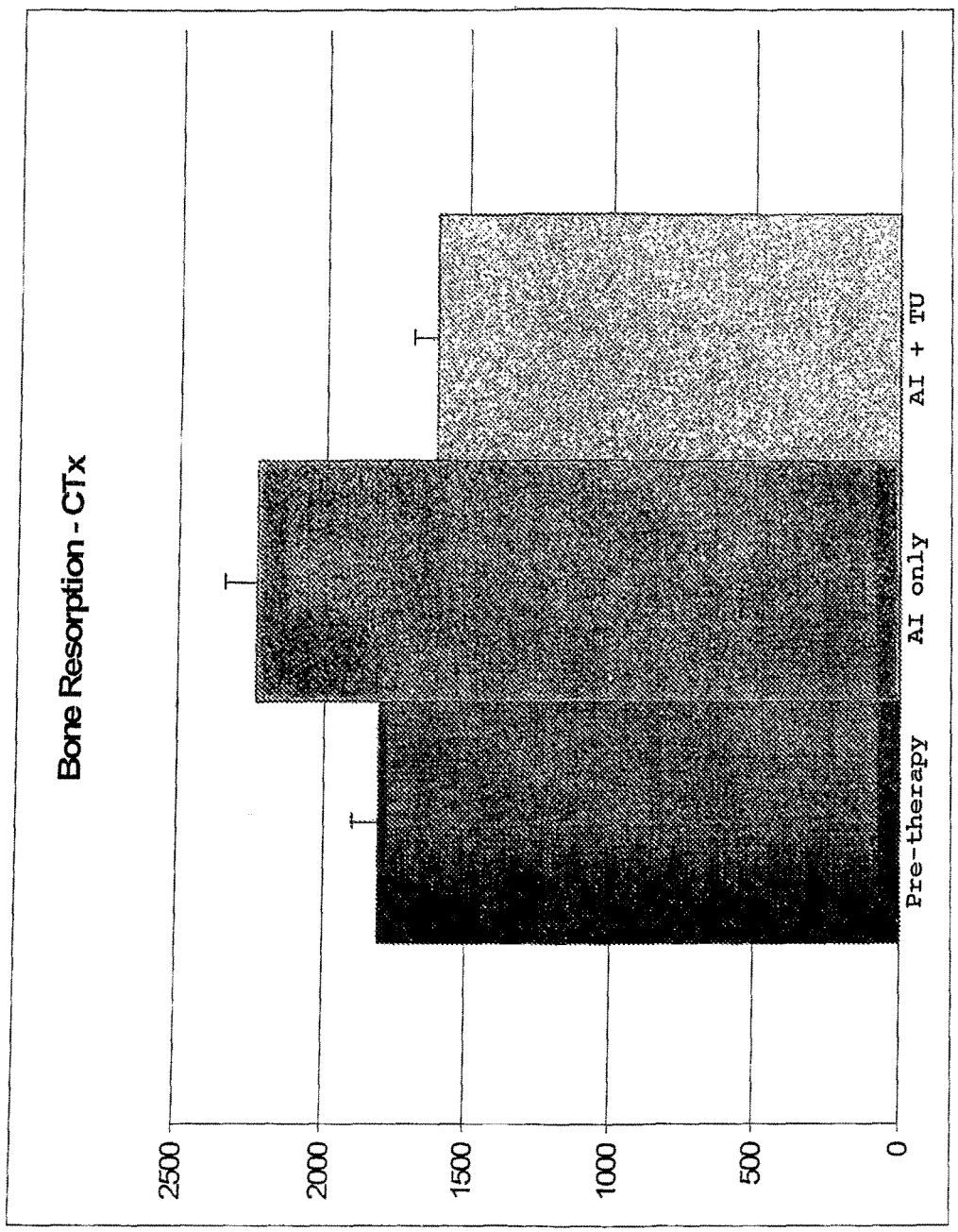
FIG. 3 is a chart demonstrating the effects of a combination of an aromatase inhibitor (Arimidex®) and an androgenic agent (testosterone undecanoate) upon serum markers for bone resorption in post-menopausal patients referred to in the example described herein.

The chart depicted in FIG. 3 depicts the effects of combination aromatase inhibitor (ARIMIDEX®) and androgenic agent (testosterone undecanoate) upon the serum markers for bone resorption during the course of this study of post-menopausal patients. The y axis is picomoles/L of serum. In particular, it is noted that measurements of carboxy-terminal collagen crosslinks ("CTx") in serum in pmol/l for the patients in the study showed that following eight weeks of combination aromatase inhibitor and androgen replacement therapy, bone resorption returned to levels experienced prior to the beginning of aromatase inhibitor therapy. In fact, while not significantly large, there even appeared to have been a small decrease in bone resorption relative to the levels measured for the post-menopausal patients prior to the beginning of any drug therapy. Measurements of carboxy-terminal collagen crosslinks were approximately 25% less in the AI+TU therapy than in the pre-therapy. Thus, the study supports the conclusion that androgen replacement therapy according to the present invention could counterbalance the undesirable bone loss side-effects associated with extended therapy with aromatase inhibitors.

Figure 4:
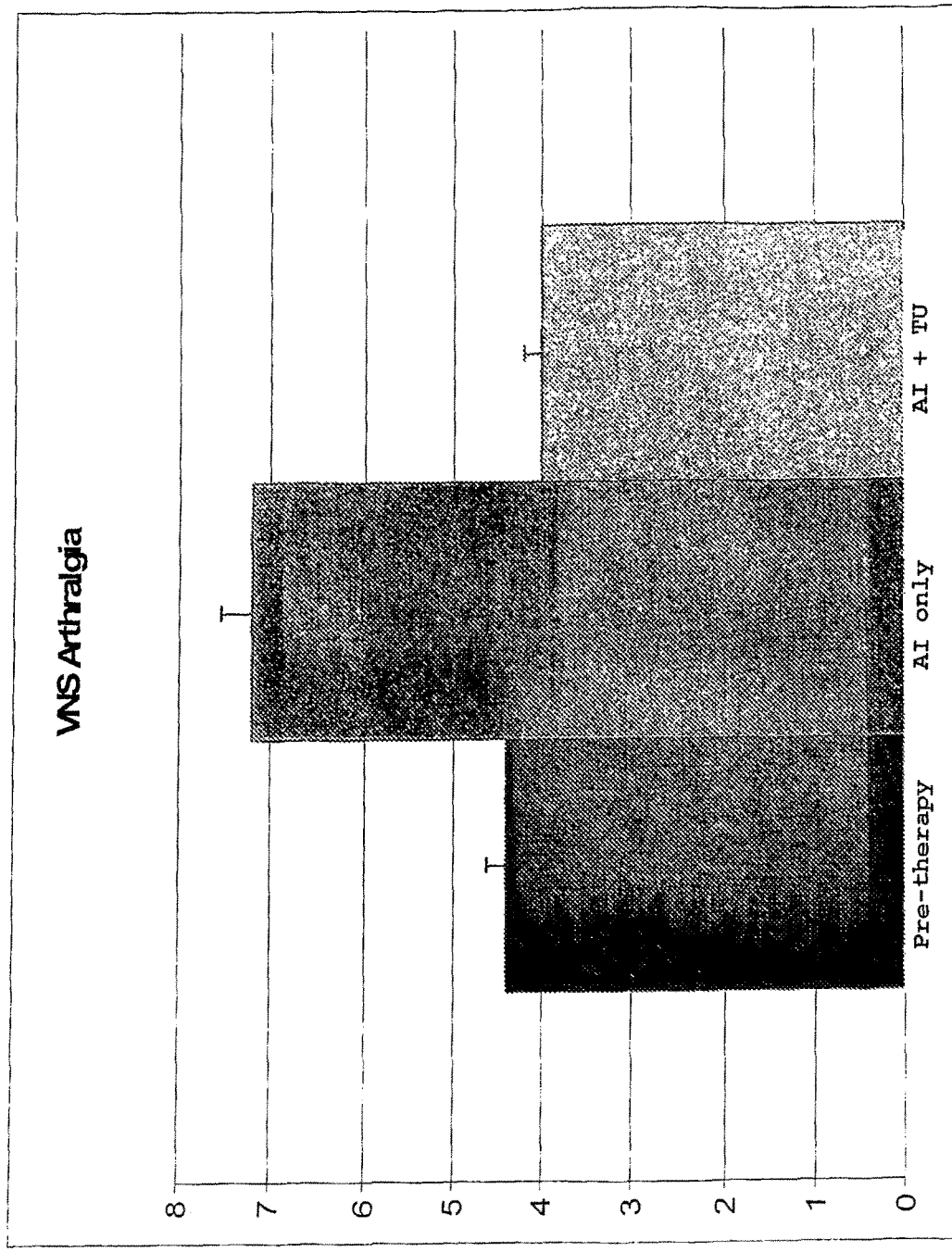
FIG. 4 is a chart demonstrating the effects of a combination of an aromatase inhibitor (Arimidex®) and an androgenic agent (testosterone undecanoate) as measured by arthralgia evaluations in post-menopausal patients referred to in the example described herein.

FIG. 4 is a chart demonstrating the effects of combination aromatase inhibitor (ARIMIDEX®) and androgenic agent (testosterone undecanoate) as measured by arthralgia evaluations in the post-menopausal patients in this study. The y axis is a visual analogue pain scale. Specifically, the y axis indicates a percentage score of a subjective quantification of pain measured out of 100. Again, the data regarding reported arthralgia symptoms by the patients in the study showed that arthralgia returned to pre-therapy levels after administration of testosterone undecanoate was added to aromatase inhibitor therapy, as opposed to elevated levels of arthralgia that were reported during administration of anastrozole only. Measurements of arthralgia were approximately 45% less in AI+TU therapy than in the pre-therapy.

Figure 5:
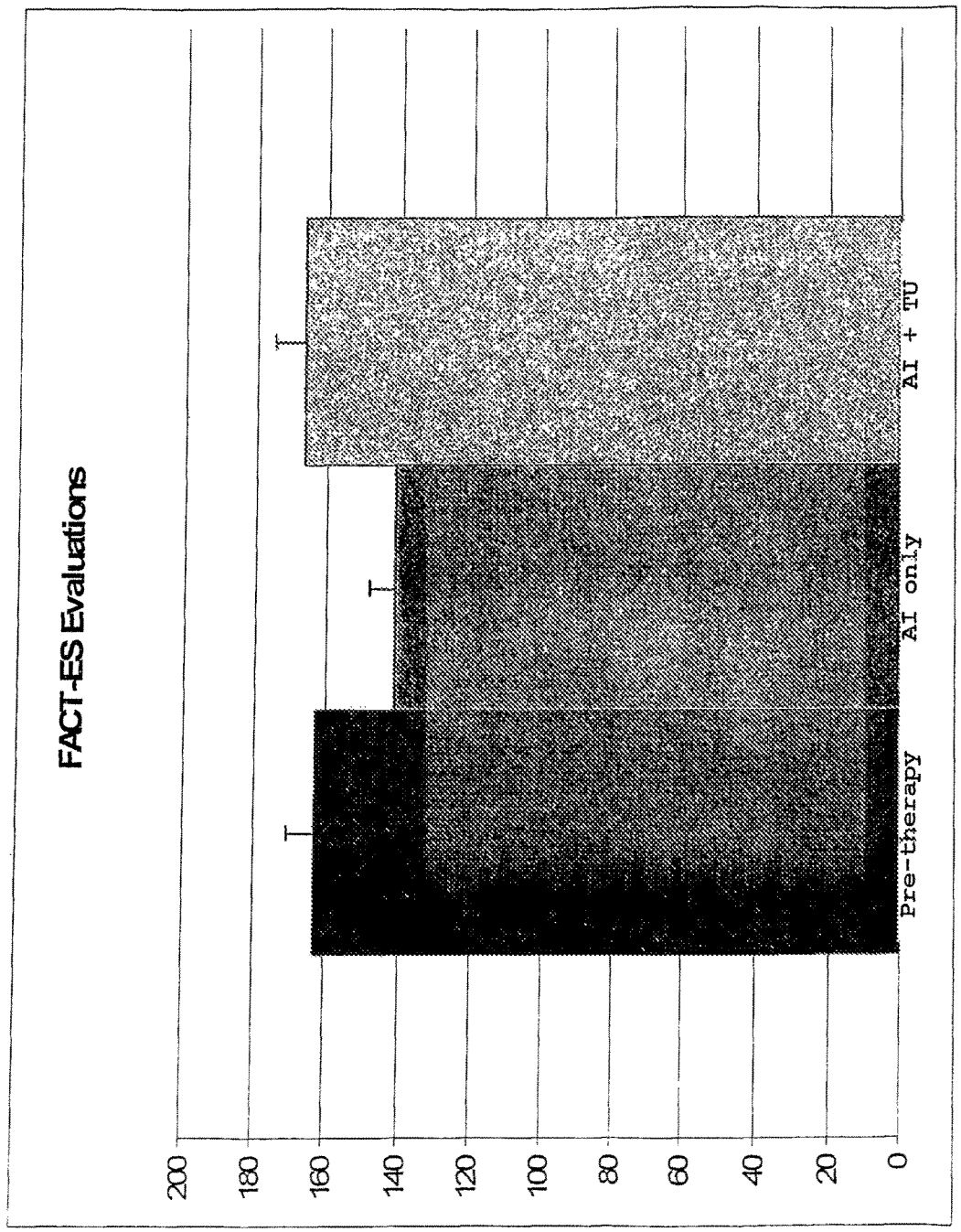
FIG. 5 is a chart demonstrating the effects of a combination of an aromatase inhibitor (Arimidex®) and an androgenic agent (testosterone undecanoate) as measured by FACT-ES side-effect profile evaluations in post-menopausal patients referred to in the example described herein.

At the three assessment times during the study, the quality of life for each patient was assessed using standard Functional Assessment of Cancer Therapy-Endocrine Symptoms (FACT-ES) questionnaire (See FIG. 8), which questionnaire is a standard method for determining the occurrence and prominence of treatment-related symptoms and side-effects in breast cancer patients. The y axis is a FACT-ES score. The total points from the FACT-ES questionnaire for each subject was subtracted from 200 to yield a FACT-ES score. A lower FACT-ES score, therefore, means the worse the symptoms. Thus, a chart provided in FIG. 5 depicts the effect of combination aromatase inhibitor (ARIMIDEX®) and androgenic agent (testosterone undecanoate) as measured by FACT-ES side-effect profile evaluations at the three assessment times in this study, with a higher FACT-ES score being associated with an overall better quality of life. The data reported in FIG. 5 shows that quality of life as measured by FACT-ES questionnaires decreased upon the patients undergoing aromatase inhibitor-only therapy, but later improved to approximate pre-therapy levels upon the introduction of testosterone undecanoate administration.

Figure 6:
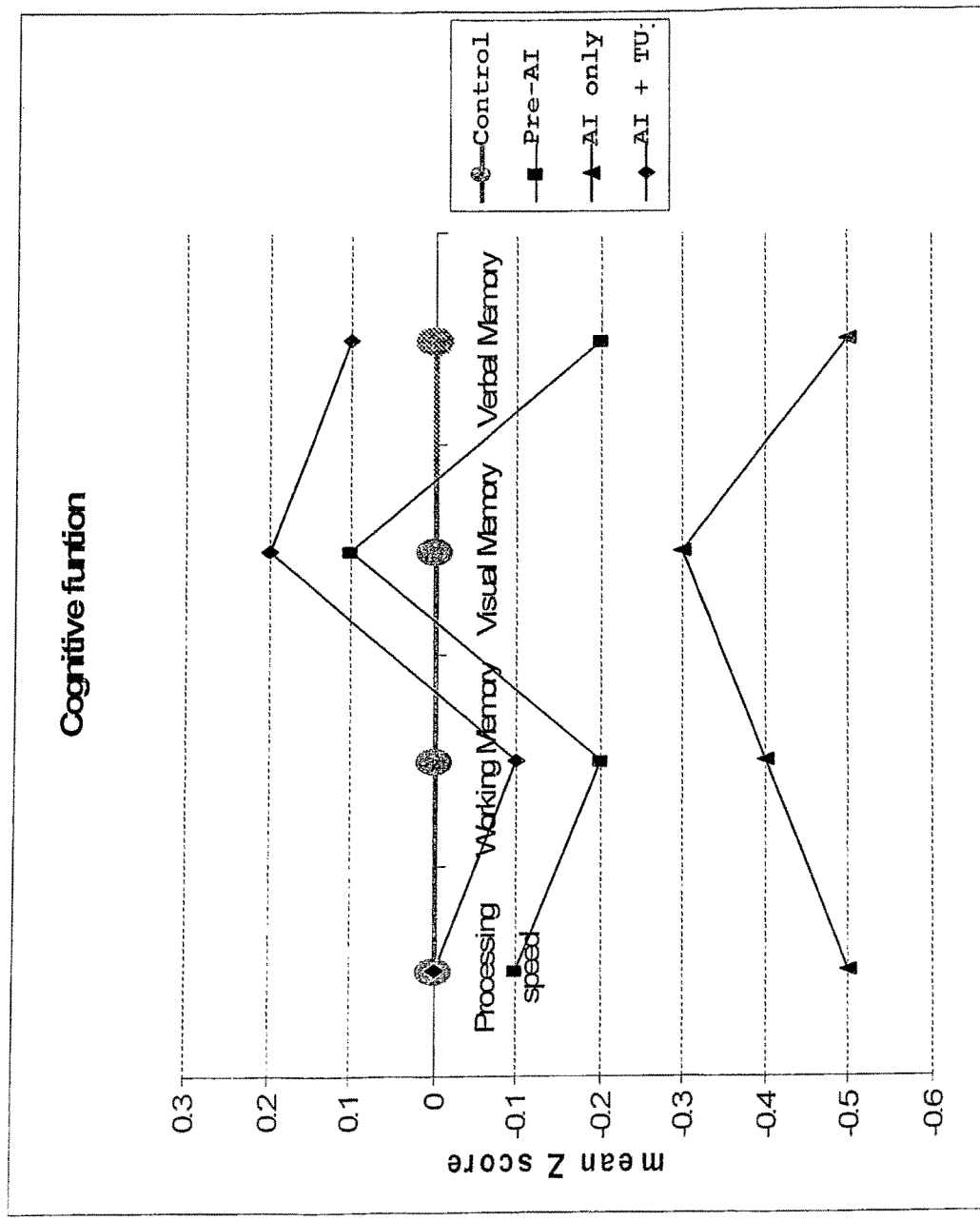
FIG. 6 is a chart demonstrating the effects of a combination of an aromatase inhibitor (Arimidex®) and androgenic agent (testosterone undecanoate) as measured by cognitive function evaluations in post-menopausal patients referred to in the example described herein.

With regard to the effect upon the cognitive function of the study patients, the chart in FIG. 6 depicts the results measured by cognitive function evaluations in the patients at each of the three different assessment times. The y axis is a mean Z score. The cognitive function scores for the study patients in the pre-therapy evaluations, as expected, varied slightly around scores for control populations in the four different types of cognitive abilities that were tested, namely processing speed, working memory, visual memory, and verbal memory. As shown in FIG. 6, the cognitive function scores for the study patients decreased across all four ability types following the four weeks of anastrozole-only therapy. Following the eight weeks of combined aromatase inhibitor and testosterone undecanoate, however, the cognitive function scores improved across all four ability types enough to restore, or even possibly slightly improve, cognitive function in the study patients. Control was five age match healthy subjects.

Figure 7:
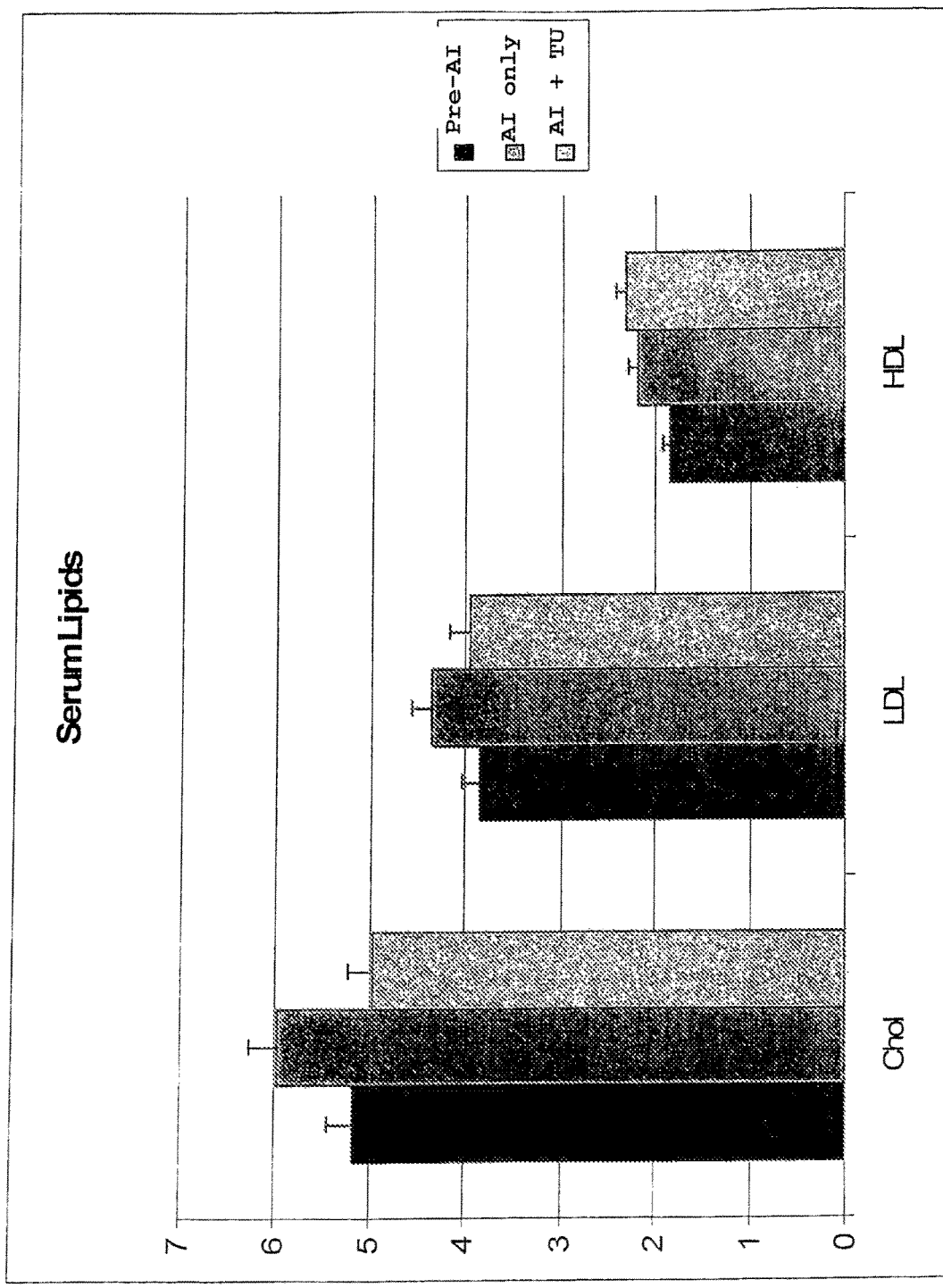
FIG. 7 is a chart demonstrating the effects of a combination of an aromatase inhibitor (Arimidex®) and an androgenic agent (testosterone undecanoate) upon serum lipid levels in post-menopausal patients referred to in the example described herein.

Finally, the chart in FIG. 7 reports the data for the study patients collected to monitor the effects of the combination aromatase inhibitor and testosterone undecanoate therapy upon serum lipid levels. The Y axis is mmol/L of serum. The results reported in the chart demonstrate that the combination therapy according to the present invention appears to raise no concerns regarding cholesterol.

Examples 2-13 (Prophetic)

The following examples demonstrate the advantages of administering to a subject diagnosed with breast cancer a pharmaceutical composition comprising an androgenic agent and/or an aromatase inhibitor, in combination or sequentially. It is to be understood that treatment of the patient with the disclosed products (both in these examples and in the rest of the specification) can be start from the first day and continued for the appropriate time period to effectively treat the patient without first administering the aromatase inhibitor by itself for a period of time. It is contemplated that the treatment period would continued for about 3 months, for about 6 months, for about 1 year, for about 2 years, for about 4 years or any longer or shorter time period that is deemed appropriate.

Example 2 (Prophetic)

Each woman selected is subjected to four weeks of aromatase inhibitor therapy with 1 mg anastrozole (ARIMIDEX®) orally as a tablet once a day, and thereafter to an additional eight weeks of the same aromatase inhibitor in combination with at least one of the following amounts of testosterone undecanoate: 20 mg, 40 mg, or 80 mg once a day. The combination of anastrozole and testosterone undecancate is administered in a single dose capsule that has crystallized anastrozole and encapsulated testosterone undecanoate in an oil suspension. The side effects associated with anastrozole treatment are measured as described in Example 1. Data are expected to show improvement of at least one or more side effects. It is to be understood that the above treatment could

Example 3 (Prophetic)

Each woman selected is subjected to four weeks of aromatase inhibitor therapy with 25 mg exemestane (AROMASIN®) orally as a tablet once a day, and thereafter to an additional eight weeks of the same aromatase inhibitor in combination with at least one of the following amounts of testosterone undecanoate: 20 mg, 40 mg, or 80 mg once a day. The combination of exemestane and testosterone undecanoate is administered in a single dose capsule that has crystallized exemestane and encapsulated testosterone undecanoate in an oil suspension. The side effects associated with exemestane treatment are measured as described in Example 1. Data are expected to show improvement of at least one or more side effects.

Example 4 (Prophetic)

Each woman selected is subjected to four weeks of aromatase inhibitor therapy with 2.5 mg letrozole (FEMARA®) orally, as a tablet once a day, and thereafter to an additional eight weeks of the same aromatase inhibitor in combination with at least one of the following amounts of testosterone undecanoate: 20 mg, 40 mg, or 80 mg once a day. The combination of letrozole and testosterone undecanoate is administered in a single dose capsule that has crystallized we need AZ comment here letrozole and encapsulated testosterone undecanoate in an oil suspension. The side effects associated with letrozole treatment are measured as described in Example 1. Data are expected to show improvement of at least one or more side effects.

Example 5 (Prophetic)

Each woman selected is subjected to four weeks of aromatase inhibitor therapy with 1 mg anastrozole (ARIMIDEX®) orally as a tablet once a day, and thereafter to an additional eight weeks of the same aromatase inhibitor in combination with at least one of the following amounts of testosterone: 20 mg, 40 mg, or 50 mg once a day. The combination of anastrozole and testosterone is administered as a tablet and an injection, a tablet and an a transdermal patch, a tablet and subcutaneously, or a tablet and a capsule, respectively. The side effects associated with anastrozole treatment are measured as described in Example 1. Data are expected to show improvement of at least one or more side effects.

Example 6 (Prophetic)

Each woman selected is subjected to four weeks of aromatase inhibitor therapy with 25 mg exemestane (AROMASIN®) orally as a tablet once a day, and thereafter to an additional eight weeks of the same aromatase inhibitor in combination with at least one of the following amounts of testosterone: 20 mg, 40 mg, or 50 mg once a day. The combination of exemestane and testosterone is administered as a tablet and an injection, a tablet and an a transdermal patch, a tablet and subcutaneously, or a tablet and a capsule, respectively. The side effects associated with exemestane treatment are measured as described in Example 1. Data are expected to show improvement of at least one or more side effects.

Example 7 (Prophetic)

Each woman selected is subjected to four weeks of aromatase inhibitor therapy with 2.5 mg letrozole (FEMARA®) orally as a tablet once a day, and thereafter to an additional eight weeks of the same aromatase inhibitor in combination with at least one of the following amounts of testosterone: 20 mg, 40 mg, or 50 mg once a day. The combination of letrozole and testosterone is administered as a tablet and an injection, a tablet and an a transdermal patch, a tablet and subcutaneously, or a tablet and a capsule, respectively. The side effects associated with letrozole treatment are measured as described in Example 1. Data are expected to show improvement of at least one or more side effects.

Example 8 (Prophetic)

Each woman selected is subjected to four weeks of aromatase inhibitor therapy with 1 mg anastrozole (ARIMIDEX®) orally as a tablet once a day, and thereafter to an additional eight weeks of the same aromatase inhibitor in combination with at least one of the following amounts of methyltestosterone: 0.5 mg, 1.25 mg, or 2.5 mg once a day. The combination of anastrozole and methyltestosterone is administered in a single dose tablet. The side effects associated with anastrozole treatment are measured as described in Example 1. Data are expected to show improvement of at least one or more side effects.

Example 9 (Prophetic)

Each woman selected is subjected to four weeks of aromatase inhibitor therapy with 25 mg exemestane (AROMASIN®) orally as a tablet once a day, and thereafter to an additional eight weeks of the same aromatase inhibitor in combination with at least one of the following amounts of methlytestosterone: 0.5 mg, 1.25 mg, or 2.5 mg once a day. The combination of exemestane and methyltestosterone is administered in a single dose tablet. The side effects associated with exemestane treatment are measured as described in Example 1. Data are expected to show improvement of at least one or more side effects.

Example 10 (Prophetic)

Each woman selected is subjected to four weeks of aromatase inhibitor therapy with 2.5 mg letrozole (FEMARA®) orally as a tablet once a day, and thereafter to an additional eight weeks of the same aromatase inhibitor in combination with at least one of the following amounts of methyltestosterone: 0.5 mg, 1.25 mg, or 2.5 mg once a day. The combination of letrozole and methyltestosterone is administered in a single dose tablet. The side effects associated with letrzole treatment are measured as described in Example 1. Data are expected to show improvement of at least one or more side effects.

Example 11 (Prophetic)

Each woman selected is subjected to four weeks of aromatase inhibitor therapy with 1 mg anastrozole (ARIMIDEX®) orally as a tablet once a day, and thereafter to an additional eight weeks of the same aromatase inhibitor in combination with at least one of the following amounts of testosterone propionate: 20 mg, 40 mg, or 80 mg once a day.

oral The combination of anastrozola and testosterone undecanoate is administered in a single dose capsule that has crystallized anastrozole and encapsulated testosterone undecanoate in an oil suspension. The side effects associated with anastrozole treatment are measured as described in Example 1. Data are expected to show improvement of at least one or more side effects.

Example 12 (Prophetic)

Each woman selected is subjected to four weeks of aromatase inhibitor therapy with 25 mg exemestane (AROMASIN®) orally as a tablet once a day, and thereafter to an additional eight weeks of the same aromatase inhibitor in combination with at least one of the following amounts of testosterone propionate: 20 mg, 40 mg, or 80 mg once a day. oral The combination of exemestane and testosterone undecanoate is administered in a single dose capsule that has crystallized exemestane and encapsulated testosterone undecanoate in an oil suspension. The side effects associated with exemestane treatment are measured as described in Example 1. Data are expected to show improvement of at least one or more side effects.

Example 13 (Prophetic)

Each woman selected is subjected to four weeks of aromatase inhibitor therapy with 2.5 mg letrozole (FEMARA®) orally as a tablet once a day, and thereafter to an additional eight weeks of the same aromatase inhibitor in combination with at least one of the following amounts of testosterone propionate: 20 mg, 40 mg, or 80 mg once a day. The combination of letrozole and testosterone undecanoate is administered in a single dose capsule that has crystallized letrozole and encapsulated testosterone undecanoate in an oil suspension. The side effects associated with letrozole treatment are measured as described in Example 1. Data are expected to show improvement of at least one or more side effects.

Pharmaceutical compositions according to this invention generally will be administered in a convenient formulation. The following formulation examples only are illustrative and are not intended to limit the scope of the present invention.

While the present invention has been described in terms of preferred embodiments in order to facilitate better understanding of the invention, it should be appreciated that various modifications can be made without departing from the principles of the invention. Therefore, the invention should be understood to include all such modifications within its scope. Numerous insubstantial variations, changes, and substitutions will now be apparent to those skilled in the art without departing from the scope of the invention disclosed herein. Accordingly, it is intended that the invention be limited only by the spirit and scope of the claims as will be allowed.

The invention claimed is:

1. A method of mitigating one or more side effects in a postmenopausal patient being treated for breast cancer, comprising administering to said patient:
   a) 30-50 mg per day of testosterone or testosterone undecanoate, or 10 mg per day of methyltestosterone; and
   b) an effective amount per day of an aromatase inhibitor; wherein the mitigated one or more side effects comprises arthritis or arthralgia.

2. The method of claim 1, wherein the testosterone, testosterone undecanoate, or methyltestosterone is administered orally.

3. The method of claim 1, wherein the testosterone is administered in tablet form.

4. The method of claim 3, wherein the tablet is administered once a day.

5. The method of claim 1, wherein 30 mg per day of testosterone is administered.

6. The method of claim 1, wherein 40 mg per day of testosterone undecanoate is administered.

7. The method of claim 1, wherein 10 mg per day of methyltestosterone is administered.

8. The method of claim 1, wherein the aromatase inhibitor is anastrozole.

9. The method of claim 8, wherein the effective amount of the anastrozole is about 1 mg per day.

10. The method of claim 8, wherein the anastrozole is administered orally.

11. The method of claim 8, wherein the anastrozole is administered in tablet form.

12. The method of claim 11, wherein the tablet is administered once a day.

13. The method of claim 8, wherein 30 mg per day of testosterone is orally administered and 1 mg per day of the anastrozole is orally administered.

14. The method of claim 1, wherein the aromatase inhibitor treatment is an adjuvant therapy treatment to said patient already having received chemotherapy.

* * * * *